United States Patent
Shin et al.

(10) Patent No.: US 9,730,872 B2
(45) Date of Patent: Aug. 15, 2017

(54) METHOD FOR IMPROVING SKIN CONDITIONS WITH VERATRIC ACID OR ACCEPTABLE SALT THEREOF AS AN ACTIVE INGREDIENT

(71) Applicant: Bio Spectrum, Inc., Seongnam-si, Gyeonggi-do (KR)

(72) Inventors: Seoung Woo Shin, Seongnam-si (KR); Eun Sun Jung, Suwon-si (KR); Deok Hoon Park, Seongnam-si (KR)

(73) Assignee: BIO SPECTRUM, INC., Seongnam-si, Gyeonggi-Do (KR)

( * ) Notice: Subject to any disclaimer, the term of this patent is extended or adjusted under 35 U.S.C. 154(b) by 0 days.

(21) Appl. No.: 15/188,366

(22) Filed: Jun. 21, 2016

(65) Prior Publication Data

US 2016/0296440 A1    Oct. 13, 2016

Related U.S. Application Data

(63) Continuation of application No. 14/437,050, filed as application No. PCT/KR2013/010907 on Nov. 28, 2013.

(30) Foreign Application Priority Data

Dec. 4, 2012  (KR) .......................... 10-2012-0139564

(51) Int. Cl.
| | |
|---|---|
| *A61K 8/368* | (2006.01) |
| *A61Q 19/00* | (2006.01) |
| *A61Q 7/00* | (2006.01) |
| *A61Q 19/08* | (2006.01) |
| *A61Q 17/04* | (2006.01) |
| *A61K 8/06* | (2006.01) |
| *A23L 33/105* | (2016.01) |

(52) U.S. Cl.
CPC ............ *A61K 8/368* (2013.01); *A23L 33/105* (2016.08); *A61K 8/06* (2013.01); *A61Q 7/00* (2013.01); *A61Q 17/04* (2013.01); *A61Q 19/00* (2013.01); *A61Q 19/08* (2013.01); *A23V 2002/00* (2013.01); *A61K 2800/48* (2013.01); *A61K 2800/524* (2013.01); *A61K 2800/74* (2013.01); *A61K 2800/92* (2013.01)

(58) Field of Classification Search
CPC .......... A61Q 17/04; A61Q 7/00; A61Q 19/00; A23L 33/105
See application file for complete search history.

(56) References Cited

U.S. PATENT DOCUMENTS

2008/0014282 A1*  1/2008  Long ...................... A61K 8/982
                                                    424/547

FOREIGN PATENT DOCUMENTS

| JP | 2003231643 A | * | 8/2003 |
|---|---|---|---|
| KR | 20040097716 A | | 11/2004 |
| KR | 20080069816 A | | 7/2008 |
| KR | 20080090160 A | | 10/2008 |
| KR | 20090021963 A | | 3/2009 |
| KR | 20090025497 A | | 3/2009 |
| KR | 20090056521 A | | 6/2009 |
| KR | 20110078678 A | | 7/2011 |
| KR | 20120039384 A | | 4/2012 |
| KR | 20120048589 A | | 5/2012 |
| KR | 20120119226 A | | 10/2012 |

OTHER PUBLICATIONS

Miyazawa, JP 2003231643 A (Aug. 2003), Espacenet English Translation, downloaded Oct. 2016.*
Boobalan Raja, et al; Veratric acid ameliorates hyperlipidemia and oxidative stress in Wistar rats fed an . . . ; Mol Cell Biochem; 2012; 366; pp. 21-30.
Murugesan Saravanakumar, et al; Veratric acid, a phenolic acid attenuates blood pressure and oxidative stress . . . ; Euro Journal of Pharmacology; 2011; 671; pp. 87-94.
Murugesan Saravanakumar, et al; Effect of veratric acid on the cardiovascular risk of . . . ; J. Cardiovasc Pharmacol; vol. 59; No. 6; Jun. 2012; pp. 553-562.
Diane Thiboutot, et al; Activity of the type 1 . . . ; J. Investigative Dermatology, Inc.; 1995; pp. 209-214.

* cited by examiner

*Primary Examiner* — Mark V Stevens
(74) *Attorney, Agent, or Firm* — Lucas & Mercanti, LLP

(57) ABSTRACT

A method for improving skin conditions containing applying a composition containing veratric acid or acceptable salt thereof as an active ingredient. The composition has an excellent effect of reducing skin wrinkles through molecular mechanisms including the promotion of collagen synthesis and inhibition of collagenase activity. Also, the composition has an excellent effect of reducing wrinkles by absorbing UVB to prevent UV rays from penetrating the skin, promotion of collagen synthesis and inhibition of collagenase activity. In addition, the composition has effect of promotion of hair growth and the prevention of hair loss through growth promotion of hair dermal papilla cells, stimulation of IGF-1 secretion, and inhibition of TGF-beta1 secretion. Also, because the composition is derived from plants such as natural materials, it is harmless to the human body and can be safely applied to cosmetic, pharmaceutical, and food compositions.

3 Claims, 4 Drawing Sheets

[Figure 1]
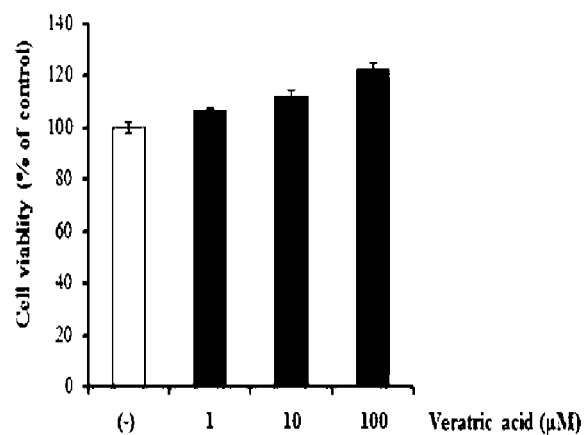
[Figure 2]
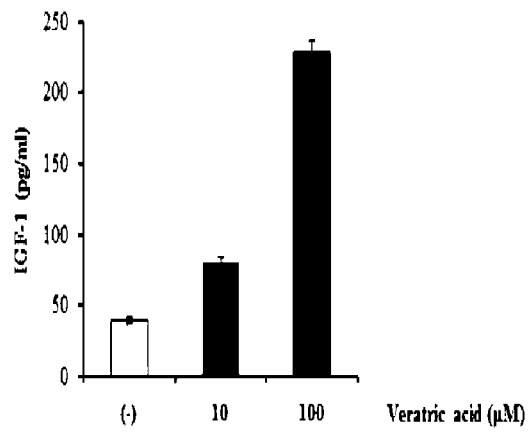

【Figure 3】
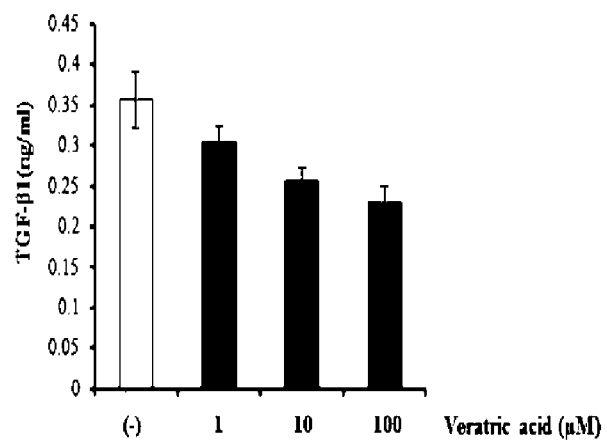
【Figure 4】
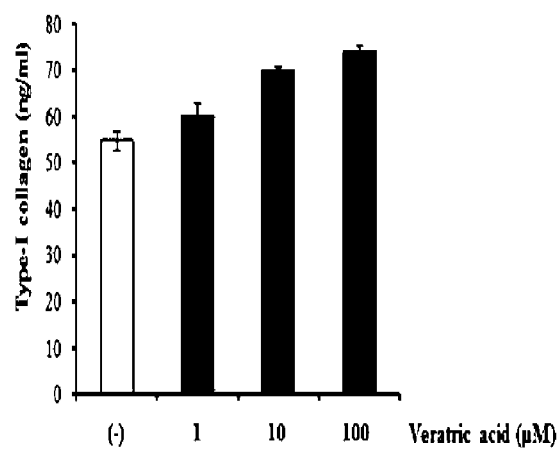

[Figure 5]
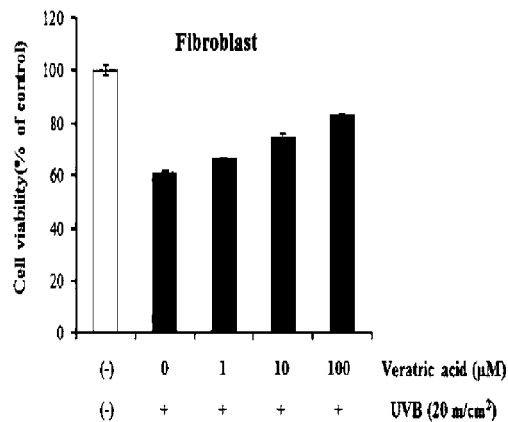
[Figure 6]
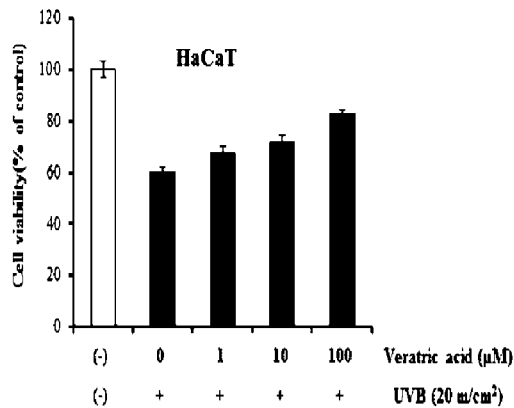

【Figure 7】
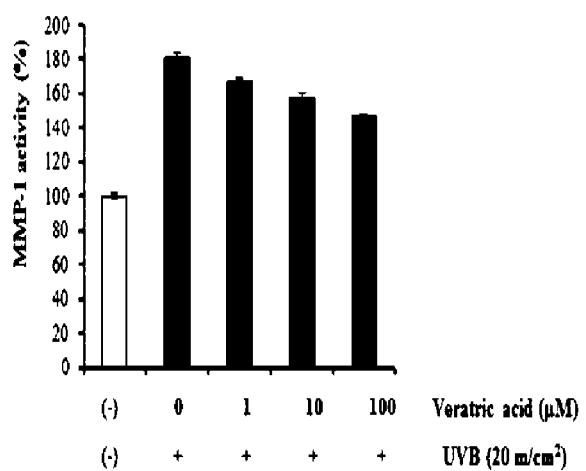

METHOD FOR IMPROVING SKIN CONDITIONS WITH VERATRIC ACID OR ACCEPTABLE SALT THEREOF AS AN ACTIVE INGREDIENT

CROSS-REFERENCE TO RELATED APPLICATIONS

This application is a continuation of U.S. patent application Ser. No. 14/437,050 filed on Apr. 20, 2015, which was a 371 of PCT/KR2013/010907, filed Nov. 28, 2013, which claimed the benefit of KR Patent Application No. 10-2012-0139564, filed Dec. 4, 2012, the priority of each of these applications is claimed and each of these applications is incorporated herein by reference.

TECHNICAL FIELD

The present invention relates to a composition comprising veratric acid or acceptable salt thereof as an active ingredient, more particularly, which has excellent stability, can be used safely without adversely affecting the skin, and has excellent effects on blocking UV rays, reducing wrinkles, promotion of hair growth and prevention of hair loss.

BACKGROUND ART

Due to environmental pollution, car exhaust gases and the like, hormone imbalance conditions are becoming severe. For this reason, the incidence of hair loss is increasing, the age of people with hair loss is decreasing, and various skin diseases are being caused due to the inability of the skin immune system. Thus, extensive studies have been conducted to develop materials that can provide a beautiful appearance and can effectively solve various phenomena that are serious social problems, for example, wrinkle formation by intrinsic aging and UV rays, immune imbalance, and hair loss.

Wrinkles are caused by aging of the skin, and aged skin is a result of the natural changes associated with the process of aging. Skin aging is roughly classified into two categories: physiological aging that shows an age-related change in the skin's function, structure or shape throughout the skin surface, and photoaging caused by UV rays.

As skin aging progresses, a significant change in the dermis appears. Dermal atrophy appearing in people 70 years of age or older is a typical aging phenomenon. Changes in the dermis result from changes in high-molecular-weight substances in the extracellular matrix due to decreases in the number of fibroblasts and the ability to form fibroblasts. Specific examples of these changes include separation of collagen bundles, a decrease in mucopolysaccharide synthesis, decreases in the number and diameter of collagen and elastin, decomposition of collagen and elastin, and blood vessel expansion. Generally, among various factors, including the skin's moisture content, collagen content and immune responses to external environments, the expression level and activity of collagenase, a collagen-degrading enzyme that reduces the production and content of collagen, has the greatest effect on the formation of wrinkles.

Methods for preventing wrinkles include a method of using an antioxidant that inhibits the generation of reactive oxygen species to prevent cell aging, a peeling method in which the skin is peeled off using chemicals such as hydroxyl acid (glycolic acid) or beta-hydroxyl acid (salicylic acid) to reduce thin wrinkles on the skin, a Botox therapy in which a specific amount of botulinum toxin is injected into wrinkled facial muscles to reduce wrinkles, and a filler method in which a wrinkled area is filled with a material such as hyaluronic acid to alleviate wrinkles.

The above methods have an insignificant effect on the alleviation of wrinkles, or when they are excessively used, they cause side effects and are problematic in terms of stability and safety. For this reason, there is a need for the development of compositions that are derived from natural materials, have less side effects, are safe, and have an excellent effect of reducing wrinkles.

The term "alopecia" refers to a state in which hairs are not present in regions which should have hair, and more particularly to loss of terminal hairs from the scalp. Alopecia (hair loss) is caused mainly by genetic factors and the male hormone androgen. Tissues associated with androgen include sebaceous gland, keratinocytes of the epidermis and hair follicle, dermal papilla cells, sweat glands, root sheath of the scalp hair follicle, etc.

It was reported that the activity of 5-α-reductase in the tissue of a region with alopecia is generally higher than that in the tissue of a region having hair. 5-α-reductase acts to reduce testosterone into dehydrotestosterone (DHT), and it is known that testosterone is involved in an increase in skeletal muscles, sperm formation and the like in the secondary sex character of males, and dehydrotestosterone is involved in acne, an increase in sebum, alopecia and benign prostatic hyperplasia (J. Invest. Dermatol. 1995; 105(2): 209-14). Thus, many studies have been conducted to find pharmacologically active substances that treat alopecia by inhibiting the activity of 5-α-reductase that is involved in the reduction of testosterone into dehydrotestosterone.

Conventional inhibitors of 5-α-reductase include compounds such as finasteride and are used as prostate therapeutic agents and alopecia preventive agents at different doses. Finasteride is excellent in terms of convenience and efficacy, but has a problem in that it is prepared using expensive or highly toxic reagents, which increase the production cost or cause environmental pollution. Particularly, it has problems in that it is not easy to remove byproducts, resulting in a decrease in the purity of the desired product, or reagents or active derivatives that are readily deteriorated by water are used, making it difficult to produce finasteride. In addition, steroidal hormones themselves play an important role in normal physiological activity, and thus when the production of steroidal hormones is artificially blocked, various problems can arise.

Thus, there is a need to develop substances that stimulate the secretion of growth factors, which stimulate the proliferation of dermal papilla cells or are helpful in the proliferation, and at the same time, inhibit the biosynthesis of TGF-beta-1 that is a signaling substance downstream of 5-α-reductase, rather than developing substances that inhibit the activity of 5-α-reductase.

With respect to methods for reducing skin wrinkles, preventing hair loss and promoting hair growth, Korean Patent Registration No. 0868784 discloses a cosmetic composition for reducing skin wrinkles, which contains an extract of *Rhodotus palmatus* cultured broth, and Korean Patent Laid-Open Publication No. 2007-0123712 discloses a cosmetic composition for preventing skin aging, which contains Rambutan and Lychee extracts as active ingredients. Further, Korean Patent Laid-Open Publication No. 2010-0119226 discloses a composition for preventing hair loss and promoting hair growth, which contains a seaweed extract, and Korean Patent Laid-Open Publication No. 2004-0097416 discloses a health functional food for preventing and ameliorating hair loss and seborrheic skin conditions, which contains an *Actinidia* extract. Moreover, Korean Patent Laid-Open Publication No. 2011-0078678 discloses a cosmetic composition for reducing wrinkles, which contains an isoflavone aglycone, and Korean Patent Laid-Open Publication No. 2008-0069816 discloses a composition for reducing skin wrinkles and improving skin elasticity, which contains a Puer tea extract. In addition, Korean Patent Laid-Open Publication No. 2009-0021963 discloses a composition for preventing hair loss and promoting hair growth, which contains, as an active ingredient, one or more of a 2-methyl-hept-2-ene derivative and linalool oxide, and Korean Patent Laid-Open Publication No. 2012-0039384 discloses a composition for promoting hair growth, which contains flavonoid.

However, a method for blocking UV rays, reducing skin wrinkles, promoting hair growth and preventing hair loss using veratric acid or acceptable salt thereof as disclosed in the present invention has not yet been disclosed.

Accordingly, the present inventors have made extensive efforts to develop a plant-derived composition for improving skin conditions, which is based on a natural material and harmless to the human body and has excellent safety, stability and effects. As a result, the present inventors have found that a composition containing veratric acid or acceptable salt thereof as an active ingredient is very effective for protection from UV rays, the reduction of skin wrinkles, the promotion of hair growth and the prevention of hair loss, thereby completing the present invention.

DISCLOSURE OF INVENTION

Technical Problem

It is an object of the present invention to provide a cosmetic composition for improving skin conditions comprising veratric acid or cosmetologically acceptable salt thereof as an active ingredient.

It is another object of the present invention to provide a pharmaceutical composition for improving skin conditions comprising veratric acid or pharmaceutically acceptable salt thereof as an active ingredient.

It is still another object of the present invention to provide a food composition for improving skin conditions comprising veratric acid or food acceptable salt thereof as an active ingredient.

Solution to Problem

In one aspect, the present invention provides a cosmetic composition for improving skin conditions comprising veratric acid or cosmetologically acceptable salt thereof as an active ingredient.

In the present invention, veratric acid of the present invention has an IUPAC name of 3,4-dimethoxybenzoic acid. It has a structure represented by the following formula 1:

[Formula 1]

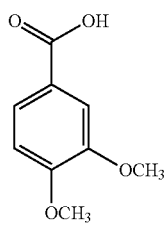

The veratric acid can be extracted, separated and purified from *Tabebuia impetiginosa, Mentha spicata*, and the like. It is known that the veratric acid has antihypertensive and antioxidant effects. In addition, it was reported that veratric acid is a candidate which inhibits the activity of HMG-CoA (3-hydroxy-3-methylglutaryl-coenzyme A) reductase to ameliorate cardiovascular disease and hyperlipidemia (Eur J Pharmacol. 2011; J Cardiovasc Pharmacol. 2012; Mol Cell Biochem. 2012).

When the veratric acid is extracted from natural plant materials with an extraction solvent. It can be extracted using an extraction solvent selected from water, an anhydrous or hydrated lower alcohol having 1 to 4 carbon atoms (methanol, ethanol, propanol, butanol and the like), a mixed solvent of the lower alcohol with water, acetone, ethyl acetate, chloroform or 1,3-butylene glycol. Preferably, it can be extracted using an aqueous solution of methanol, ethanol, or butanol, and more preferably, it can be extracted using an aqueous solution of butanol.

Moreover, the veratric acid can be obtained by a conventional purification process, in addition to the extraction method employing the extraction solvent. For example, the veratric acid also be obtained from fractions obtained through various additional purification methods, including separation with an ultrafiltration membrane having a given molecular weight cut-off, and separation by various chromatography systems (manufactured for separation according to size, charge, hydrophobicity or affinity).

In the present invention, a cosmetologically acceptable salt of veratric acid may be acid addition salts produced by cosmetologically acceptable free acids or metal salts produced by bases. For one example, the free acids may be organic acids and inorganic acids. Particular examples of the inorganic acids may include hydrochloric acid, sulfuric acid, bromic acid, sulfurous acid, or phosphoric acid, and the organic acids may include citric acid, acetic acid, maleic acid, fumaric acid, glyconic acid, or methanesulfonic acid. Furthermore, particular examples of the metal salts may include alkali metal salt or alkaline earth metal salt, sodium, potassium, or calcium salts. But it is not limited thereto.

In the present invention, the term improving skin conditions means a protection from UV rays, reduction in skin wrinkles, promotion of hair growth and prevention of hair loss.

In the present invention, cosmetic composition comprising veratric acid or cosmetologically acceptable salt thereof as an active ingredient exhibits an excellent effect of reducing skin wrinkles through molecular mechanisms including the protection of fibroblasts, promotion of collagen synthesis and inhibition of collagenase activity.

In one specific example, keratinocytes (HaCaT) and fibroblasts were irradiated with UVB, and then cell viability was examined under various concentration of veratric acid. As a result, it was found that cell viability increased as the concentration of veratric acid increased. This suggests that veratric acid the effect of protect skin cells from UV-rays.

In another specific example, the rate of increase of collagen synthesis in human normal fibroblasts was examined under various concentration of veratric acid. As a result, it was found that collagen synthesis increased as the concentration of veratric acid increased. This suggests that veratric acid exhibits the effect of reducing wrinkles by synthesizing collagen.

In still another specific example, when human normal fibroblasts were irradiated with UVB, collagen synthesis and collagenase activity were examined under various concentration of veratric acid. As a result, it was shown that, the increased collagenase activity by UVB irradiation was reduced under various concentration of veratric acid. In addition, the reduced collagen synthesis by UVB irradiation was increased under various concentration of varatric acid. This suggests that veratric acid has the effect of preventing wrinkles.

In still another specific example, a cosmetic composition containing veratric acid was applied to the human skin and the elasticity of the skin was observed. As a result, it was found that the skin elasticity increased as the content of veratric acid in the cosmetic composition was increased. It suggests that veratric acid has the effect of reducing wrinkles.

In the present invention, cosmetic composition comprising veratric acid or cosmetologically acceptable salt thereof exhibits the effect of promoting hair growth and preventing hair loss by proliferation of hair follicle dermal papilla cell, stimulation of insulin-like growth factor-1 (IFG-1) secretion, and inhibition of transforming growth factor-beta1 (TGF-beta1) synthesis.

In one specific example, the cell viability of human hair follicle dermal papilla cells was examined under various concentration of varatric acid. As a result, it was found that the viability of hair follicle dermal papilla cells increased as the concentration of veratric acid increased. It suggests that veratric acid exhibits the effect of promoting hair growth by proliferating hair follicle dermal papilla cells. Also, hair growth agent containing veratric acid was administered into alopecia during 6 months. As a result, it was shown that the group administered with veratric acid had the bristle hairs including downy hairs started to appear from 1 or 2 months after treatment with the present composition. In addition, it was exhibited better effect of hair growth in the high content of veratric acid. Therefore, veratric acid has the effect of promoting hair growth.

In another specific example, the IFG-1 and TGF-beta1 synthesis in human hair follicle dermal papilla cells was examined under various concentration of veratric acid. As a result, it was found that IFG-1 synthesis was increased and TGF-beta1 was synthesis reduced as the concentration of veratirc acid increased. This suggests that veratric acid has the effect of preventing hair loss.

The cosmetic composition of the present invention may contain, in addition to veratric acid or cosmetologically acceptable salt thereof as an effective ingredient which exhibits the effect of protection from UV rays, reduction in skin wrinkles, promotion of hair growth and prevention of hair loss, components that are conventionally used in cosmetic compositions. Examples of the components include conventional auxiliaries, such as antioxidants, stabilizers, solubilizers, vitamins, pigments and fragrances, and carriers.

The cosmetic composition of the present invention may be prepared into a solution, a suspension, an emulsion, a paste, a gel, a cream, a lotion, a powder, a soap, a surfactant-containing cleanser, an oil, a powdered foundation, an emulsion foundation, a wax foundation, a spray, or the like. But it is not limited there to. More specifically, the cosmetic composition may be formulated into a nutrient cream, a lotion astringent, a softening toner, a lotion, an essence, a shampoo, a nutrient gel, or massage cream.

If the formulation of cosmetic composition is a paste, a cream, or a gel, it may contain, as carrier components, animal oil, vegetable oil, wax, paraffin, starch, tragacanth, cellulose derivatives, polyethylene glycol, silicon, bentonite, silica, talc, or zinc oxide.

If the formulation of cosmetic composition is a powder or a spray, it may contain, as carrier components, lactose, talc, silica, aluminum hydroxide, calcium silicate or polyamide powder. Particularly, if it is spray, it may additionally contain a propellant, such as chlorofluorohydrocarbon, propane/butane, or dimethyl ether.

If the formulation of cosmetic composition is a solution or an emulsion, it may contain, as carrier components, a solvent, a solubilizing agent or an emulsifing agent. The examples thereof include water, ethanol, isopropanol, ethyl carbonate, ethyl acetate, benzyl alcohol, benzyl benzoate, propylene glycol, 1,3-butyl glycol oil, glycerol-aliphatic ester, polyethylene glycol, or sorbitan-aliphatic ester.

If the formulation of cosmetic composition is a suspension, it may contain, as carrier components, a liquid diluent, such as water, ethanol, or propylene glycol, a suspending agent, such as ethoxylated isostearyl alcohol, polyoxyethylene sorbitol ester, or polyoxyethylene sorbitan ester, microcrystalline cellulose, aluminum metahydroxide, bentonite, agar, or tragacanth.

If the formulation of cosmetic composition is a surfactant-containing cleanser, it may contain, as carrier components, aliphatic alcohol sulfate, aliphatic alcohol ester sulfate, sulfosuccinic acid monoester, isethionate, imidazolium derivatives, methyl taurate, sarcosinate, fatty acid amide ether sulfate, alkyl amidobetaine, aliphatic alcohol, fatty acid glyceride, fatty acid acid diethanolamide, vegetable oil, lanolin derivatives, or ethoxylated glycerol fatty acid ester.

The veratric acid or cosmetologically acceptable salt thereof according to the present invention is contained in the composition in an amount of 0.00001-15 wt %, preferably 0.0001-10 wt %, and more preferably 0.0001-5 wt %, based on the total weight of the cosmetic composition. If the content of veratric acid in the composition is less than 0.00001 wt %, the effect of protection from UV rays, reduction in skin wrinkles, promotion of hair growth and prevention of hair loss will be insignificant, and if the content of veratric acid is more than 15 wt %, an increase in the effect, which results from an increase in the content of veratric acid, will be insignificant and the stability of a formulation comprising veratric acid will not be ensured.

In case the inventive composition comprising veratric acid or cosmetologically acceptable salt thereof as an active ingredient is used, it shows effects of reducing skin wrinkles by protection of fibroblast, increase of collagen synthesis or inhibition of collagenase active. Also, it shows effects of promoting hair growth and preventing hair loss by growth promotion of hair dermal papilla cell, stimulation of IGF-1 secretion and inhibition of TGF-beta1 secretion.

In another aspect, the present invention provides a pharmaceutical composition for improving skin conditions comprising veratric acid or pharmaceutically acceptable salt thereof as an active ingredient.

The structures of veratric acid, their extract method, and their effects in the present invention, are same as described above.

Also, in the present invention, the term improving skin conditions are same as described above.

In the present invention, a pharmaceutically acceptable salt of veratric acid may be acid addition salts produced by pharmaceutically acceptable free acids or metal salts produced by bases. For one example, the free acids may be organic acids and inorganic acids. Particular examples of the inorganic acids may include hydrochloric acid, sulfuric acid, bromic acid, sulfurous acid, or phosphoric acid, and the organic acids may include citric acid, acetic acid, maleic acid, fumaric acid, glyconic acid, or methanesulfonic acid. Furthermore, particular examples of the metal salts may include alkali metal salt or alkaline earth metal salt, sodium, potassium, or calcium salts. But it is not limited thereto.

The pharmaceutical composition of the present invention may contain, in addition to veratric acid or pharmaceutically acceptable salt thereof as an effective ingredient which exhibits the effect of protection from UV rays, reduction in skin wrinkles, and promotion of hair growth and prevention of hair loss, components that are conventionally used in pharmaceutical compositions. Examples of the components include a lubricant, a wetting agent, a sweetener, a flavoring agent, an emulsifier, a suspending agent, a preservative, and carriers.

The pharmaceutically acceptable carriers of the present invention is lactose, dextrose, sucrose, sorbitol, mannitol, starch, acacia rubber, potassium phosphate, alginate, gelatin, calcium silicate, microcrystalline cellulose, polyvinylpyrrolidone, cellulose, water, syrups, methyl cellulose, methylhydroxy benzoate, propylhydroxy benzoate, talc, magnesium stearate, and mineral oils, but are not limited to. Details of suitable pharmaceutically acceptable carriers and formulations can be found in Remington's Pharmaceutical Sciences (19th ed., 1995), which is incorporated herein by reference.

The pharmaceutical composition of the present invention may be administered orally or parenterally. Preferably, it is administered parenterally, and most preferably, it is administered by topical application.

The pharmaceutical composition of the present invention is administered in a pharmaceutically effective amount. As used herein, the term pharmaceutically effective amount refers to an amount sufficient to treat or prevent diseases, at a reasonable benefic/risk ratio applicable to any medical treatment or prevention. The effective dosage level may be determined depending on various factors, including the disease's type and the disease severity, the activity of the drug, the patient's age, bodyweight, health, gender, the patient's sensitivity to the drug, the time of administration of the extract used, the route of administration, the excretion rate, the duration of treatment, a drug which is combined or used simultaneously with the extract, and other factors known in the medical field. Generally, the suitable dose is preferably applied once to several times a day in the range of 0.001-100 mg/kg for an adult. When the composition is a preparation for external use, it is preferably applied 1 to 5 times a day in amount of 1.0-3.0 ml for 1 month or more for an adult. However, the above-described dose of the composition does not limit the scope of the present invention.

The pharmaceutical composition may be formulated using a pharmaceutically acceptable carrier and/or excipient according to a method known to those skilled in the art, so that it can be prepared as a unit dosage form or included in a multi-dosage container. According to the intended therapeutic purpose, the pharmaceutical composition may be formulated into pharmaceutical preparations common in the pharmaceutical field. For examples, the formulations include tablets, capsules, elixirs, granules, suspensions, emulsions, syrups, plasters, ointments, sprays, oils, gels, spirits, tinctures, baths, liniments, lotions, patches, pads, and creams. Topical formulations are preferably used for direct application of the composition to a desired area of the external surface of the skin. Preferred topical formulations include ointments, lotions, sprays, and gels. Topical formulations may be contained in a support base or matrix directly applicable to a desired area of the skin. Examples of the support base include gauze or bandages.

The veratric acid or pharmaceutically acceptable salt thereof according to the present invention is contained in the composition in an amount of 0.00001 to 15 wt %, preferably 0.0001 to 10 wt %, and more preferably 0.0001 to 5 wt %, based on the total weight of the pharmaceutically composition. If the content of veratric acid in the composition is less than 0.00001 wt %, the effect of protection from UV rays, reduction in skin wrinkles, promotion of hair growth and prevention of hair loss will be insignificant, and if the content of veratric acid is more than 15 wt %, an increase in the effect, which results from an increase in the content of veratric acid, will be insignificant and the stability of a formulation comprising veratric acid will not be ensured.

In case the inventive composition comprising veratric acid or pharmaceutically acceptable salt thereof as an active ingredient is used, it shows effects of reducing wrinkles by protection of fibroblast, increase of collagen synthesis or inhibition of collagenase active. Also, it shows effects of promoting hair growth and preventing hair loss by growth promotion of hair dermal papilla cell, stimulation of IGF-1 secretion and inhibition of TGF-beta1 secretion.

In another aspect, the present invention provides a food composition for reducing wrinkles and preventions comprising veratric acid or food acceptable salt thereof as an active ingredient.

The structures of veratric acid, their extract method, and their effects in the present invention, are same as described above.

In the present invention, a food acceptable salt of veratric acid may be acid addition salts produced by food acceptable free acids or metal salts produced by bases. For one example, the free acids may be organic acids and inorganic acids. Particular examples of the inorganic acids may include hydrochloric acid, sulfuric acid, bromic acid, sulfurous acid, or phosphoric acid, and the organic acids may include citric acid, acetic acid, maleic acid, fumaric acid, glyconic acid, or methanesulfonic acid. Furthermore, particular examples of the metal salts may include alkali metal salt or alkaline earth metal salt, sodium, potassium, or calcium salts. But it is not limited thereto.

In one specific example, veratric acid was administered orally into UV-irradiated hairless mice, and the effect thereof was examined. As a result, it was shown that the group administered with veratric acid had the effect of preventing wrinkles.

When the inventive composition is used as a food composition, it may comprise, in addition to the active ingredient veratric acid or food acceptable salt thereof, components which are generally added in the preparation of foods. For example, it includes proteins, carbohydrates, fats, nutrients, seasonings, and flavoring agents. The carbohydrate may be, for example, a monosaccharides, e.g., glucose, fructose, etc., disaccharide, e.g., maltose, sucrose, oligosaccharide, etc., a polysaccharide, e.g., dextrin, cyclodextrian, etc., or a sugar alcohol, e.g., xylitol, sorbitol, erithritol, etc. The flavor may be a natural flavor (thaumatin, stevia extract (e.g., rebaudioside A, glycyrrhizin, etc.)) or a synthetic flavor (saccharin, aspartame, etc.).

There is no particular limit to the kind of food composition. Examples of foods to which veratric acid or food acceptable salt thereof can be added include meats, sausages, bread, chocolates, candies, snacks, confectionery, pizza, a ramen, noodles, gum, dairy products including ice-cream, various soups, beverages, teas, drinks, alcohol beverages, and multi-vitamin preparations. The health foods include all health foods in a conventional sense.

When the health food of the present invention is a health beverage, it may additionally contain various sweetening agents or natural carbohydrates as in conventional beverages. The natural carbohydrates include monosaccharides, such as glucose and fructose, disaccharides, such as maltose and sucrose, natural sweeteners, such as dextrin and cyclodextrin, and synthetic sweeteners, such as saccharin and aspartame. The natural carbohydrates are used in an amount of about 0.01-0.04 g, and preferably about 0.02-0.03 g, based on 100 ml of the health beverage of the present invention.

In addition, the health food of the present invention may contain various nutrients, vitamins, electrolytes, flavoring agents, colorants, pectic acid and its salt, alginic acid and its salt, organic acids, protective colloidal thickeners, pH adjusters, stabilizers, preservatives, glycerin, alcohol, carbonating agents used in carbonated drinks, etc. Additionally, the health food of the present invention may contain fruit flesh for the preparation of natural fruit juices, fruit juice beverages and vegetable juices. These components may be used alone or in combination. Although not critical, these additives are used in an amount of 0.01-0.1 parts by weight based on 100 parts by weight of the health food of the present invention.

The veratric acid or food acceptable salt thereof of the present invention is contained in the composition in an amount of 0.00001 to 15 wt %, preferably 0.0001 to 10 wt %, and more preferably 0.0001 to 5 wt %, based on the total weight of the cosmetic material composition. If the content of veratric acid in the composition is less than 0.00001 wt %, the effect of protection from UV rays, reduction in skin wrinkles, promotion of hair growth and prevention of hair loss will be insignificant, and if the content of veratric acid is more than 15 wt %, an increase in the effect, which results from an increase in the content of veratric acid, will be insignificant and the stability of a formulation comprising veratric acid will not be ensured.

When the composition comprising veratric acid or food acceptable salt thereof as an active ingredient is used, it can exhibit the effect of reducing wrinkles by increasing collagen synthesis or reducing collagenase activity.

In one specific example, the veratric acid was applied to the human skin and the cumulative skin irritation of the skin was observed. As a result, it was found that veratric acid which is the natural substance was harmless to the human body. Therefore, veratric acid of the present invention may be used with confidence for a long period, because it has little or no toxicity and adverse effect. Particularly, it may be used safely in the above-described cosmetic, pharmaceutical and food compositions.

The present invention also provides a method of improving the skin conditions of a subject by administering said composition to the subject.

As used herein, the term "subject" is meant to include humans and mammals, for example, dogs, pigs, horses and cattle, in which poor skin conditions, for example, wrinkles, skin darkening and hair loss, are to be improved or prevented, and the purpose can be achieved by administering the composition of the present invention.

As used herein, the term "administering" means introducing a given substance into a subject according to any suitable method. The composition of the present invention may be administered orally or parenterally through any general route, so long as it can reach a target tissue. In addition, the composition of the present invention may be administered by any device which delivers the active ingredient into a target, for example, a cell.

Those skilled in the art will understand from the above description and the following examples that skin conditions or abnormal conditions resulting therefrom can be improved, ameliorated, prevented or treated by administering the composition of the present invention to a subject using the above-described methods.

Advantageous Effects

As described above, the inventive cosmetic, pharmaceutical, and food composition containing veratric acid or acceptable salt thereof as an active ingredient has the effect of protection from UV rays, the reduction of skin wrinkles, the promotion of hair growth or the prevention of hair loss. In addition, it has no cytotoxicity, which causes no adverse effects on the skin, and thus can be safely used as a cosmetic, pharmaceutical and food compositions.

BRIEF DESCRIPTION OF DRAWINGS

FIG. 1 shows the proliferation rate of hair follicle dermal papilla cells under various concentration of veratirc acid.

FIG. 2 shows the secretion rate of IGF-1 under various concentration of veratric acid.

FIG. 3 shows the inhibition rate of TGF-beta1 as a function of the concentration of veratric acid.

FIG. 4 shows the synthesis of collagen under various concentration of veratric acid when human normal fibroblasts were irradiated with UVB.

FIG. 5 shows the viability of cell under various concentration veratric acid when fibroblasts were irradiated with UVB.

FIG. 6 shows the viability of cell under various concentration veratric acid when keratinocytes were irradiated with UVB.

FIG. 7 is shows collagenase activity under various concentration of veratric acid when human normal fibroblasts were irradiated with UVB.

BEST MODE

Hereinafter, the present invention will be described in further detail with reference to examples. It is to be understood, however, that these examples are for illustrative purposes and are not intended to limit the scope of the present invention.

Example 1: Preparation of Hair Growth Agent

A hair growth agent containing varatric acid was prepared as a hydrogel base having the component and contents shown in Table 1 below. Concretely, an aqueous phase comprising purified water was dissolved by heating to 70° C., and oil phase comprising a preservative and a thickener was dissolved by heating to 70° C., thus preparing an emulsion using homixer (Tokushu Kika, Japan). Then, the emulsion was cooled to 45° C., and veratric acid was added to an amount of 0.1 and 1.0 wt % on the total weight of the composition and dispersed in the cooled emulsion, followed by cooling to 30° C. In Table 1, test groups 1 and 2 are hair growth agent containing veratric acid.

TABLE 1

| Component | Content (%) | |
|---|---|---|
| | Test group 1 | Test group 2 |
| Veratric acid | 0.1 | 1.0 |
| Preservative (Gramben) | 0.5 | 0.5 |
| Thickener (xanthan-gum) | 0.3 | 0.3 |
| Purified water | 99.1 | 98.2 |
| Total weight | 100 | 100 |

Example 2: Measurement of Effects on Hair Growth and Hair Loss Prevention of Veratric Acid 2-1. Measurement of Effects on Hair Growth and Hair Loss Prevention Under Invitro Conditions Human hair follicle dermal papillar cells (Application, Inc., USA) were seeded into a 6-well micro plate containing DMEM medium (Gibco, USA) with FBS at a density of $3 \times 10^5$ cells per well, and then were cultured in a 5% $CO_2$ incubator at 37° C. for 24 hours. The next day, the cells were washed once with serum-free medium, and the medium was replaced with serum-free medium. Then, the cells were treated with 0, 10 and 100 μM of veratric acid, followed by incubating for 72 hours, after which the cells were washed once with serum-free medium, the medium was replaced with serum-free medium containing 10% MTT, and after 3 hours, the optical density (O.D.) value was measured and calculated as a percentage of control. The results are shown in FIG. 1.

As a result, veratric acid increased the proliferation of human hair follicle dermal papilla cells in a concentration-dependent manner.

2-2. Measurement of Effects on Hair Growth and Hair Loss Prevention Under Invivo Conditions 40 hair loss patients (age: 40s to late 60s) were divided into the following four groups each consisting of 10 persons: alopecia patients having follicular atrophy and baldness; typical male-pattern alopecia patients; and acute alopecia areata patients. Each of the hair loss compositions prepared in Example 1 was applied to the hair loss portion of each alopecia patient twice a day in an amount of 3 cc each time for 6 months. The conditions of hair loss and hair growth were observed at 1-month intervals. In a comparative group, Moxidil (Hanmi Pharm Co., Ltd., Korea) was used, and in a control group, 50% ethanol alone was used. The results are shown in Table 2 below.

The criteria of evaluation were as follows:
4: having high effect=new hairs appear
3: having moderate effect=new hairs (downy hairs) appear
2: having slight effect=degree of hair loss decreases
1: having no effect=no change appears

TABLE 2

|  | Control group | Comparative group | Test group 1 | Test group 2 |
|---|---|---|---|---|
| Efficacy/effect | 1.6 | 4.3 | 2.7 | 3.4 |

As shown in Table 2 above, in the alopecia patients treated with the hair loss compositions containing veratric acid of the present invention, bristle hairs including downy hairs started to appear from 1 or 2 months after treatment with the compositions. 6 months after treatment with the compositions, the hair growth effect was shown 80% of the patients. In addition, it was observed that new hairs grew continuously and no hair loss phenomenon was found.

Example 3: Measurement of Effects of Veratric Acid on Inducing Growth Factor IGF-1

Human hair follicle dermal papillar cells (Application, Inc., USA) were seeded into a 24-well micro plate at density of 7.5×10$^4$ cells per well, and then were cultured in a 5% $CO_2$ incubator at 37° C. for 24 hours. Then, the medium was replaced with serum-free medium, followed by being cultured for 16 hours. Then, each well was treated with 0, 10 and 100 μM of veratric acid, after which the cells were incubated for 48 hours. Then, the cell culture media were collected.

The secretion rate of growth factor insulin-like growth factor-1 (IGF-1) was determined by measuring the amount of secretion rate of IGF-1 using Insulin-like growth factor-1 quantikine ELISA kit (DG100, R&D system, USA). The results are shown in FIG. 2.

As a result, veratric acid increased the IGF-1 secretion of human hair follicle dermal pailla cells in a concentration-dependent manner.

Example 4: Measurement of Effects of Veratric Acid on the Inhibition of TGF-Beta1 Production Human hair follicle dermal papillar cells (Application, Inc., USA) were seeded into a 24-well micro plate at a density of 7.5×10$^4$ cells per well, and then were cultured in a 5% $CO_2$ incubator at 37° C. for 24 hours. Then, the medium was replaced with serum-free medium, followed by being cultured for 16 hours. Then, each well was treated with 0, 10 and 100 μM of veratric acid, after which the cells were incubated for 48 hours. Then, the cell culture media were collected.

The secretion rate of transforming growth factor-beta1 (TGF-beta1) was determined by measuring the amount of secretion rate of TGF-beta1 using Human LAP TFG-beta1 ELISA kit (ab100647, abcam, USA). The results are shown in FIG. 3.

As a result, veratric acid excellently inhibited TGF-beta1 production, as veratric acid suppressed the expression of TGF-beta1. It is suggested that veratric acid has hair growth promoting effects.

Example 5: Measurement of Wrinkle-Reducing Effect of Veratric Acid

Human normal fibroblasts (Department of Dermatology, Ajou University) were seeded into a 24-well micro plate containing DMEM medium at a density of about 2×10$^5$ cells per well, and were cultured in a 5% $CO_2$ incubator at 37° C. for 24 hours. Then, the medium was removed from each well of the plate, and each well was treated with 0, 1, 10 and 100 μM concentrations of veratric acid, after which the cells were cultured for 24 hours. Then, the cell medium was collected, thereby preparing samples.

The amounts of collagen synthesis in the above-prepared samples was determined by measuring the amount of procollagen type I C-peptide (PICP) using a Procollagen Type I C-peptide EIA kit (MK101; Takara, Kyoto, Japan). The results are shown in FIG. 4.

As a result, veratric acid increased collagen synthesis, and collagen synthesis in human normal fibroblasts was increased as the concentration of veratric acid was increased. It is suggested that the collagen synthesis was dependent on the veratric acid concentration.

Example 6: Measurement of UV-Preventing Effect of Veratric Acid

Keratinocyte (HaCaT) and fibroblast were cultured in DMEM medium containing penicillin-streptomycin and serum. Then, the cells were seeded into a 12-well micro plate at density of about 1×10$^5$ cells per well, and were cultured in a 5% $CO_2$ incubator at 37° C. until the cells attached about 80% over on well-area. Then, each well was pretreated with 0, 1, 10 and 100 μM of veratric acid, and after 24 hours, the medium was replaced with PBS, and then the cells were irradiated with UV (UVB 20 mJ/cm$^2$). Then, the UV-irradiated cells were replaced DMEM medium containing penicillin-streptomycin and serum, the cells were incubated for 48 hours. The cell viability was determined by measuring the viability of keratinocyte (HaCaT) and fibroblast using a MTT assay (30-1010K, ATCCTM). The results are shown in FIGS. 5 and 6.

As a result, veratric acid prevented cell death of UV-induced kerationcyte and fibroblasts. Veratric acid increased the preventing rate of cell death in a concentration-dependent manner.

Example 7: Measurement of Effects of Veratric Acid on the Inhibition of Collgenase Production Human normal fibroblasts (Department of Dermatology, Ajou University) were seeded into a 24-well micro plate containing DMEM medium at a density of about $2 \times 10^5$ cells per well, and were then cultured in a 5% $CO_2$ incubator at 37° C. for 24 hours. Then, the medium was removed from each well, and the cells were treated with 0, 1, 10 and 100 µM concentrations of veratric acid. Then, the cells were cultured for 24 hours, after which the cell culture media were collected, thereby preparing samples.

The inhibition effects of collagenase production was determined by measuring the amount of collagenase using MMP-1 ELISA kit (QIA55, Merck, Germany). The results are shown in FIG. 7.

As a result, veratric acid decreased collgenase production in human normal fibroblasts. Veratric acid decreased the amounts of collagenase production in human normal fibroblast in a concentration-dependent manner.

Example 8: Measurement of Wrinkle-Reducing Effect of Cosmetic Composition Containing Veratric Acid 8-1. Preparation of Nourishing Creams Containing Veratric Acid The nourishing cream having the composition and contents shown in Table 3 below was prepared. Specifically, an aqueous phase including purified water, triethanolamine, and propylene glycol was dissolved by heating to 70° C., and an oily phase including fatty acid, oily components, an emulsifier, and a preservative was dissolved by heating to 70° C. and added to the aqueous phase. Then, the resulting solution was cooled to 45° C., and veratric acid was added with in amounts of 0, 0.01, 0.05 and 1 wt % based on the total weight of the composition and was dispersed, followed by cooling to 30° C.

TABLE 3

| Component | Content (wt %) |
|---|---|
| veratric acid | 0.01, 0.05 or 1.00 |
| Jojoba oil | 5.0 |
| Liquid paraffin | 7.0 |
| Cetylaryl alcohol | 2.0 |
| Polyglyceryl-3-methylglucose disterate | 2.0 |
| Glyceryl stearate | 0.5 |
| Squalane | 3.0 |
| Propylene glycol | 4.0 |
| Glycerine | 5.0 |
| Triethanolamine | 0.3 |
| Carboxyvinylpolymer | 0.3 |
| Tocopheryl acetate | 0.2 |
| Preservative and fragrance | Trace |
| Purifired water | Balance |
| Sum | 100 |

8-2. Measurement of Wrinkle-Reducing Effect of Cosmetic Composition Containing Veratric Acid In the measurement of skin elasticity, nourishing creams described in Preparation Example 8-1 was applied to the face of 30 healthy women of 21 to 42 years old twice a day for 3 months. The control group was used nourishing cream containing purified water.

The effect on wrinkle reduction was evaluated by measuring a change in skin elasticity. The measurement of skin elasticity was performed with Coutometer SEM 474 (Courage+Khazaka, Cologne, Germany) under the conditions of constant temperature of 24~26° C. and constant humidity of 38-40%. The evaluation criteria were as follows 0 indicating no improvement in skin elasticity, and 5 indicating improvement in skin elasticity. The results are shown in Table 4 below.

TABLE 4

| | Veratric acid (wt %) | | | |
|---|---|---|---|---|
| | 0.01 | 0.05 | 1 | 0 |
| Skin elasticity | 2.81 | 3.12 | 3.36 | 2.59 |

As a result, the use of the nourishing creams containing veratric acid showed significantly excellent skin elasticity compared to the nourishing cream containing no veratric acid. Also, the skin elasticity was increased in a concentration-dependent manner as the concentration veratric acid was increased.

Example 9: Effect of Preventing Wrinkles by Oral Administration

In order to measure the wrinkle-preventing effect of veratric acid, 6-7-week-old hairless mice (Skh: HR-1) were divided into a control group, a UV group and a UV/veratric acid group, each consisting of 8 animals, and were bred during the test period. The control group and the UV group were administered orally with 0.5 ml of saline, and the UV/veratric acid group was administered orally with a solution of 100 mg per kg veratric acid in 0.5 ml of saline.

The above-prepared samples were administered orally at the same point of time for 5 days a week for a total of 5 weeks. From 2 weeks to 5 weeks after oral administration, the UV group and the UV/veratric acid group were irradiated with UV light three times a week such that the total dose of UV radiation reached 600 mJ/cm$^2$.

To measure the wrinkle-preventing effect of veratric acid, skin replicas were taken from the back of the hairless mice using a silicon polymer before autopsy. In the same manner, after 5 weeks, skin replicas were taken from the groups treated with each of the samples. Using the taken skin replicas, the antiaging effect, i.e., wrinkle-reducing effect of each sample was measured. The results are shown in Table 5 below.

TABLE 5

| R-parameter | Control group | UV group | UV/veratric acid group |
|---|---|---|---|
| R1 value | 0.435 ± 0.0120 | 0.481 ± 0.009 | 0.462 ± 0.013 |
| R2 value | 0.357 ± 0.0105 | 0.424 ± 0.010 | 0.405 ± 0.011 |
| R3 value | 0.212 ± 0.0097 | 0.237 ± 0.008 | 0.219 ± 0.012 |
| R4 value | 0.098 ± 0.0086 | 0.138 ± 0.014 | 0.116 ± 0.010 |
| R5 value | 0.231 ± 0.013 | 0.318 ± 0.010 | 0.290 ± 0.013 |

R1 value: Skin roughness,
R2 value: Maximum roughness,
R3 value: Average roughness,
R4 value: Smoothness depth,
R5 value: Arithmetic average roughness (International Journal of Cosmetic Science, 2005 Jun; 27(3): 155-60).

As a result, when the hairless mice were irradiated with UV light, all the R1, R2, R3, R4 and R5 values indicative of wrinkles was increased. In addition, it was observed that R-parameter value was reduced in veratric acid-administered hairless mice compared to the UV/control groups.

Example 10: Safety Test of Veratric Acid on Human Skin 10-1. Preparation of Skin External Formulation Containing Veratric Acid In order to confirm whether veratric acid is safe for human skin, a veratric acid-containing skin external formulation having the components and contents shown in Table 6 was prepared, and then a skin safety verification test was carried out. Specifically, purified water, glycerin, and butylene glycol were mixed and dissolved at a temperature of 70° C. (aqueous phase). The remaining components except for the above three components and trimethanolamine were dissolved at a temperature of 70° C. (oil phase). The oil phase was added to the aqueous phase, and stirred with a homo-mixer (Tokushu Kika, Japan) to prepare an emulsion, and trimethanolamine was added thereto. Then, bubbles produced in the mixture were removed, after which the mixture cooled to room temperature, thereby preparing skin external formulations.

TABLE 6

| Component | Content (wt %) | | | |
|---|---|---|---|---|
| | Test group 1 | Test group 2 | Test group 3 | Control group |
| Purified water | 71 | 71 | 71 | 71 |
| Glycerin | 8.0 | 8.0 | 8.0 | 8.0 |
| Butylene glycol | 4.0 | 4.0 | 4.0 | 4.0 |
| Veratric acid | 0.1 | 0.5 | 1.0 | 0 |
| Caprylic/capric triglyceride | 8.0 | 8.0 | 8.0 | 8.0 |
| Squalane | 5.0 | 5.0 | 5.0 | 5.0 |
| Cetearyl glucoside | 1.5 | 1.5 | 1.5 | 1.5 |
| Sorbitan stearate | 0.4 | 0.4 | 0.4 | 0.4 |
| Cetearyl alcohol | 1.0 | 1.0 | 1.0 | 1.0 |
| Trimethanolamine | 0.1 | 0.1 | 0.1 | 0.1 |
| Total | 100 | 100 | 100 | 100 |

10-2. Cumulative Irritation Test

Each of the skin external formulations prepared in Example 10-1 was applied every other day to the forearms of 30 healthy adults and allowed to stand for 24 hours. This was repeated so that each subject was treated with 9 fresh patches in total, so as to confirm whether veratric acid irritates the skin. Control group was used to a skin external formulation containing no veratric acid on squalane base.

The patch test was performed using a Finn chamber (Epitest Ltd, Finland). The external formulations were added dropwise to the chamber in an amount of 15 μl per patch. At every round of the patch application, the response of the skin was scored using the following empirical formula 1. The results are shown in Table 7 below.

Average response degree=[[Response index×Response degree/Total number of subjects×Highest score (4 points)]×100]/Number of examinations    [empirical formula 1]

In regard to the response degree, 1 point was provided for ±, 2 points for +, and 4 points for ++. When the average response degree was less than 3, the composition was determined to be safe for use on the skin.

TABLE 7

| | Number of subjects showing response | | | | | | | | | |
|---|---|---|---|---|---|---|---|---|---|---|
| | Week 1 | | | Week 2 | | | Week 3 | | | |
| Test material | $1^{st}$ ±/+/++ | $2^{st}$ ±/+/++ | $3^{st}$ ±/+/++ | $1^{st}$ ±/+/++ | $2^{st}$ ±/+/++ | $3^{st}$ ±/+/++ | $1^{st}$ ±/+/++ | $2^{st}$ ±/+/++ | $3^{st}$ ±/+/+/+ | Average response degree |
| Control group | 1/−/− | −/−/− | −/−/− | −/−/− | −/−/− | −/−/− | −/−/− | −/−/− | −/−/− | 0.09 |
| Test group 1 | −/−/− | −/−/− | −/−/− | −/−/− | −/−/− | −/−/− | −/−/− | −/−/− | −/−/− | 0.00 |
| Test group 2 | −/−/− | −/−/− | −/−/− | −/−/− | −/−/− | −/−/− | −/−/− | −/−/− | −/−/− | 0.00 |
| Test group 3 | 1/−/− | −/−/− | −/−/− | −/−/− | −/−/− | −/−/− | −/−/− | −/−/− | −/−/− | 0.09 |
| Number of subjects | 30 | 30 | 30 | 30 | 30 | 30 | 30 | 30 | 30 | |

As a result, in the control group, the subjects corresponding to ±, +, and ++ numbered 1, 0 and 0, respectively, in the first patch, and no skin response appeared after the second patch. In the test group 1 and test group 2 to which veratric acid was 0.1 wt % and 0.5 wt % applied, no skin response appeared in all patches. In the test group 3 to which veratric acid was 1.0 wt % applied, the subjects corresponding to ±, +, and ++ numbered 1, 0 and 0, respectively, in the first patch, and no skin response appeared after the second patch. The average reactive levels in control group and test group 3 were 0.09, respectively, and the average reactive levels in test groups 1 and 2 were 0.00, respectively. Control group, test group 1, test group 2 and test group 3 are all less than 3, suggesting that the composition of the present invention is safe for use on human skin.

Formulation Example 1: Cosmetic Formulations 1-1. Preparation of Skin Softener

Shown in Table 8 below, a skin softener contacting veratric acid as an active ingredient was prepared according to a conventional method.

TABLE 8

| Component | Content (wt %) |
| --- | --- |
| Veratric acid | 0.01 |
| Glycerin | 3.0 |
| Butylene glycol | 2.0 |
| Propylene glycol | 2.0 |
| Carboxyvinyl polymer | 0.1 |
| Ethanol | 10.0 |
| Triethanolamine | 0.1 |
| Preservative, pigment, fragrance, and purified water | Balance |
| Total | 100.0 |

1-2. Preparation of Nourishing Softener

Shown in Table 9 below, a nourishing softener containing veratric acid as an active ingredient was prepared according to a conventional method.

TABLE 9

| Component | Content (wt %) |
| --- | --- |
| Veratric acid | 0.01 |
| Beeswax | 4.0 |
| Polysorbate 60 | 1.5 |
| Sorbitan sesquioleate | 0.5 |
| Liquid paraffin | 5.0 |
| Squalane | 5.0 |
| caprylic/capric triglyceride | 5.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Preservative, pigment, fragrance, and purified water | Balance |
| Total | 100.0 |

1-3. Preparation of Nourishing Cream

Shown in Table 10 below, a nourishing cream containing veratric acid as an active ingredient was prepared according to a conventional method.

TABLE 10

| Component | Content (wt %) |
| --- | --- |
| Veratric acid | 0.01 |
| Beeswax | 10.0 |
| Polysorbate 60 | 1.5 |
| Sorbitan sesquioleate | 0.5 |
| Liquid paraffin | 10.0 |
| Squalane | 5.0 |
| caprylic/capric triglyceride | 5.0 |
| Glycerin | 5.0 |
| Butylene glycol | 3.0 |
| Propylene glycol | 3.0 |
| Triethanolamine | 0.2 |
| Preservative, pigment, fragrance, and purified water | Balance |
| Total | 100.0 |

1-4. Preparation of Massage Cream

Shown in Table 11 below, a massage cream containing veratric acid as an active ingredient was prepared according to a conventional method.

TABLE 11

| Component | Content (wt %) |
| --- | --- |
| Veratric acid | 0.01 |
| Beeswax | 10.0 |
| Polysorbate 60 | 1.5 |
| Sorbitan sesquioleate | 0.8 |
| Liquid paraffin | 40.0 |
| Squalane | 5.0 |
| caprylic/capric triglyceride | 4.0 |
| Glycerin | 5.0 |
| Butylene glycol | 3.0 |
| Propylene glycol | 3.0 |
| Triethanolamine | 0.2 |
| Preservative, pigment, fragrance, and purified water | Balance |
| Total | 100.0 |

1-5: Preparation of Pack

Shown in Table 11 below, a pack containing veratric acid as an active ingredient was prepared according to a conventional method.

TABLE 12

| Component | Content (wt %) |
| --- | --- |
| Veratric acid | 0.01 |
| Polyvinyl alcohol | 13.0 |
| Sodium carboxymethyl cellulose | 0.2 |
| Allantoin | 0.1 |
| Ethanol | 5.0 |
| Nonyl phenyl ether | 0.3 |
| Preservative, pigment, fragrance, and purified water | Balance |
| Total | 100.0 |

Preparation Example 2: Preparation of Pharmaceutical Formulations

2-1: Preparation of Powder Formulation

The components shown in Table 13 below were mixed with each other and then filled in a sealed bag, thereby preparing a powder formulation containing veratric acid as an active ingredient.

TABLE 13

| Component | Content (g) |
| --- | --- |
| Veratric acid | 2 |
| Lactose | 1 |

2-2: Preparation of Tablet Formulation

The components shown in Table 14 below were mixed with each other and then compressed to a tablet according to a conventional method, thereby preparing a tablet formulation containing veratric acid as an active ingredient.

TABLE 14

| Component | Content (mg) |
| --- | --- |
| Veratric acid | 100 |
| Corn starch | 100 |
| Lactose | 100 |
| Magnesium stearate | 2 |

2-3: Preparation of Capsule Formulation

The components shown in Table 15 below were mixed with each other and then filled into a gelatin capsule according to a conventional method, thereby preparing a capsule formulation containing veratric acid as an active ingredient.

TABLE 15

| Component | Content (mg) |
|---|---|
| Veratric acid | 100 |
| Corn starch | 100 |
| Lactose | 100 |
| Magnesium stearate | 2 |

What is claimed is:

1. A method for reducing skin wrinkles, comprising:
   applying topically a composition comprising veratric acid or a salt thereof as an active ingredient to a person in need of reducing skin wrinkles,
   wherein the composition contains the veratric acid or salt thereof in an amount of 0.01-1.0 wt % based on the total weight of the composition.

2. The method of claim 1, wherein the composition has a formulation selected from the group consisting of a solution, a suspension, an emulsion, a paste, a gel, a cream, a lotion, a powder, a soap, a surfactant-containing cleanser, an oil, a powder foundation, an emulsion foundation, a wax foundation, and a spray.

3. A method for promoting hair growth comprising:
   applying topically a composition comprising veratric acid or a salt thereof as an active ingredient to a person in need of promoting hair growth,
   wherein the composition contains the veratric acid or salt thereof in an amount of 0.01-1.0 wt % based on the total weight of the composition.

* * * * *